(12) United States Patent
Gill (10) Patent No.: US 8,995,760 B2
(45) Date of Patent: Mar. 31, 2015

(54) METHOD AND APPARATUS FOR COLOURING A COSMETIC COVERING

(75) Inventor: Hugh Gill, Paisley (GB)

(73) Assignee: Touch Bionics Limited, Livingston (GB)

( * ) Notice: Subject to any disclaimer, the term of this patent is extended or adjusted under 35 U.S.C. 154(b) by 357 days.

(21) Appl. No.: 13/502,753

(22) PCT Filed: Dec. 22, 2010

(86) PCT No.: PCT/GB2010/052192
§ 371 (c)(1),
(2), (4) Date: May 21, 2012

(87) PCT Pub. No.: WO2011/077156
PCT Pub. Date: Jun. 30, 2011

(65) Prior Publication Data
US 2012/0229828 A1   Sep. 13, 2012

(30) Foreign Application Priority Data

Dec. 24, 2009 (GB) .................................. 0922603.6

(51) Int. Cl.
*G06K 9/00* (2006.01)
*A61F 2/50* (2006.01)

(52) U.S. Cl.
CPC ........ *A61F 2/5046* (2013.01); *A61F 2002/5001* (2013.01)
USPC ........................................................ 382/162

(58) Field of Classification Search
None
See application file for complete search history.

(56) References Cited

U.S. PATENT DOCUMENTS

| 5,785,960 | A | | 7/1998 | Rigg et al. | |
|---|---|---|---|---|---|
| 5,852,675 | A | * | 12/1998 | Matsuo et al. | ................ 382/167 |
| 6,111,973 | A | * | 8/2000 | Holt et al. | ..................... 382/100 |

(Continued)

FOREIGN PATENT DOCUMENTS

| EP | 0256643 A2 | 2/1988 |
|---|---|---|
| EP | 0947899 A2 | 10/1999 |

(Continued)

OTHER PUBLICATIONS

PCT International Preliminary Report on Patentability and Written Opinion of International Searching Authority for International Patent Application No. PCT/GB2010/052192, mailed Jul. 5, 2012, 7 pages.

(Continued)

*Primary Examiner* — Sean Motsinger
(74) *Attorney, Agent, or Firm* — K&L Gates LLP (57) ABSTRACT

The invention provides a method and apparatus for coloring a cosmetic covering. The apparatus includes image acquisition apparatus (18) operative to acquire an image of a part of a human or animal body to provide a digital color image, processing apparatus (20) operative to determine a calibration transform for colors of an image acquired by the image acquisition apparatus, the processing apparatus being further operative to transform the digital color image with the calibration transform to provide a color compensated digital color image, pigment mixing apparatus (26) operative to mix a plurality of pigments of different colors in dependence on at least one color characteristic of at least one color within the color compensated digital color image to produce at least one mixed pigment, and pigment applying apparatus (24) operative to apply the at least one mixed pigment to a cosmetic covering.

22 Claims, 5 Drawing Sheets

(56) References Cited

U.S. PATENT DOCUMENTS

| | | |
|---|---|---|
| 2001/0023058 A1* | 9/2001 | Jung et al. .................. 433/29 |
| 2002/0016631 A1 | 2/2002 | Marchitto et al. |
| 2004/0078299 A1* | 4/2004 | Down-Logan et al. ......... 705/27 |
| 2005/0093997 A1* | 5/2005 | Dalton et al. ............. 348/227.1 |
| 2006/0029909 A1* | 2/2006 | Kaczkowski .................. 434/98 |
| 2006/0054782 A1* | 3/2006 | Olsen et al. ................ 250/208.1 |
| 2006/0229755 A1* | 10/2006 | Kuiken et al. ................... 700/98 |
| 2006/0251408 A1* | 11/2006 | Konno et al. .................. 396/14 |
| 2007/0058860 A1* | 3/2007 | Harville et al. .............. 382/167 |
| 2007/0061111 A1 | 3/2007 | Jung et al. |
| 2007/0071314 A1 | 3/2007 | Bhatti et al. |
| 2007/0230832 A1 | 10/2007 | Usui et al. |
| 2008/0260218 A1 | 10/2008 | Smith et al. |
| 2009/0213379 A1* | 8/2009 | Carroll et al. ................ 356/405 |
| 2012/0004884 A1* | 1/2012 | Fillol et al. .................... 702/150 |
| 2012/0014571 A1* | 1/2012 | Wong et al. .................. 382/128 |
| 2012/0099788 A1* | 4/2012 | Bhatti et al. .................. 382/167 |
| 2012/0229828 A1* | 9/2012 | Gill ............................... 358/1.9 |

FOREIGN PATENT DOCUMENTS

| | | |
|---|---|---|
| GB | 2067074 A | 7/1981 |
| JP | 07174631 A | 7/1995 |
| JP | 2001299448 A | 10/2001 |
| JP | 2002131135 A | 5/2002 |
| JP | 2003134526 A | 5/2003 |
| JP | 2004073802 A | 3/2004 |
| WO | WO-0104838 A1 | 1/2001 |
| WO | WO-2006058190 A2 | 6/2006 |
| WO | WO-2006092604 A2 | 9/2006 |

OTHER PUBLICATIONS

Lickel, Andreas, "International Search Report" for PCT/GB2010/052192, a mailed Apr. 29, 2011, 4 pages.

* cited by examiner

METHOD AND APPARATUS FOR COLOURING A COSMETIC COVERING

CROSS REFERENCE TO RELATED APPLICATIONS

This is the national phase under 35 U.S.C. §371 of International Application No. PCT/GB2010/052192, filed on Dec. 22, 2010, which claims priority to and the benefit of United Kingdom Patent Application No. 0922603.6, filed on Dec. 24, 2009, the entire disclosures of each of which are incorporated by reference herein.

FIELD OF THE INVENTION

The present invention relates to a method and apparatus for colouring a cosmetic covering and in particular, but not exclusively, a method and apparatus for colouring a cosmetic covering for a prosthesis.

BACKGROUND OF THE INVENTION

Cosmetic coverings for prostheses are normally coloured to provide as life-like appearance as possible. One approach involves a clinician determining the appropriate colouring for a cosmetic covering by eye, e.g. by viewing the skin of the prosthesis wearer, and mixing differently coloured paints to achieve a match to the determined colours. The paint may be mixed from a palette consisting, for example, of eighty-four colours with each colour having two hundred and fifty six shades. The clinician then paints the cosmetic covering by hand. However, there is often no high degree of consistency in the colours from palette to palette. Also, clinicians will often see colours differently on account of a colour vision deficiency on the part of the clinician or on account of artificial lighting being used when the clinician is viewing the skin of the prosthesis wearer to determine the appropriate colouring. This approach typically results in 30% of painted cosmetic coverings being rejected.

Another approach involves a clinician taking colour readings with a spectrophotometer at six to ten different locations on the prosthesis wearer's skin to determine appropriate colours for a cosmetic covering. The colour values, e.g. Red, Blue, Yellow (RBY) values, for each location are determined by a computer from the spectrophotometer readings and differently coloured paints are mixed in dependence on the determined colour values.

The present inventor has appreciated shortcomings of the above known approaches.

According to a first aspect of the present invention, there is provided a method of colouring a cosmetic covering, the method comprising:
  determining a calibration transform for colours of an image acquired by image acquisition apparatus;
  acquiring an image of a part of a human or animal body with the image acquisition apparatus to provide a digital colour image;
  transforming the digital colour image with the calibration transform to provide a colour compensated digital colour image
  conveying at least one colour characteristic of at least one colour within the colour compensated digital colour image to a pigment mixing apparatus, which is operative to mix a plurality of pigments of different colours in dependence on the at least one colour characteristic to produce at least one mixed pigment; and
  applying the at least one mixed pigment to a cosmetic covering.

In use, an image of a part of a human or animal body, such as the left hand of person who wears a prosthetic right hand, is acquired with the image acquisition apparatus to provide a digital colour image of the part. The digital colour image may be a two dimensional digital colour image. The digital colour image may stored as a two dimensional digital array. Thus and in contrast to the known approach using the spectrophotometer, a digital colour image is obtained rather than a number, e.g. six to ten, colour readings from the human or animal body part. The colours represented in the digital colour image are liable to differ from the true colour values of the human or animal body part on account of the characteristics of the image acquisition apparatus or the lighting when the image is acquired. Hence, the steps of determining the calibration transform for the image acquisition apparatus and transforming the digital colour image with the calibration transform to provide a colour compensated digital colour image compensates for inaccuracies of the image acquisition apparatus in representing colours.

The cosmetic covering may be configured to cover a prosthesis, such as a hand prosthesis, or foot prosthesis, for example. More specifically, the cosmetic covering may be a surface of the cosmetic covering. In one form, the at least one mixed pigments may be applied by a person, e.g. using a brush. In another form, the at least one mixed pigments may be applied by pigment applying apparatus, such as spray painting apparatus.

More specifically, the method further comprises: acquiring an image of a colour chart with the image acquisition apparatus to provide a colour chart image; and determining the calibration transform in dependence on the colour chart image and colour values represented in the colour chart. The present step may be carried out under substantially the same conditions, e.g. in terms of at least one of lighting and image acquisition apparatus configuration, as the step of acquiring the image of the body part. More specifically, the colour chart may comprise a plurality of areas, with each area containing a different colour, e.g. according to a standard. Thus, the colour chart may be a Gretag MacBeth colour chart.

Alternatively or in addition, the calibration transformation may comprise a transformation for each of Red, Green and Blue values. The calibration transformation may have the form of a Look Up Table (LUT) for each of Red, Green and Blue. A LUT may have been determined by sparsely populating the LUT with differences between image colour values and actual colour values. A LUT may be populated by interpolation between sparse values contained in the LUT. Values in a LUT may be filtered. The LUT values may be filtered by at least one of: a point fitting curve, such as a Catmull-ROM point fitting curve; and a rolling average filter, such as a rolling average filter with twelve taps.

Alternatively or in addition, the method may comprise acquiring a plurality of different images of the part of the human or animal body. For example, where the part is a hand, an image of the top of the hand, an image of the bottom (i.e. palm side) of the hand and an image of the thumb side of the hand may be acquired. Hence, each of the plurality of acquired digital colour images may be transformed by the calibration transform.

Alternatively or in addition, the method may further comprise disposing the part of the human or animal body in relation to the image acquisition apparatus and displaying an image of the part acquired by the image acquisition apparatus on display apparatus, such as on a Visual Display Unit (VDU). The present step may be carried out before the step of acquiring an image of the part to provide the digital colour image. Hence, the present step may be used to determine whether or not the part is properly disposed in relation to the image acquisition apparatus and, if not, the part may be moved or its orientation changed to achieve proper disposition.

Alternatively or in addition, the method may comprise receiving the body part in an enclosed space.

More specifically, the enclosed space may be illuminated in a controlled fashion by means of a light source. Alternatively or in addition, the enclosed space may be illuminated by a light source configured to provide for substantially uniform illumination in a plane, e.g. a plane extending generally perpendicular to a path between the image acquisition apparatus and the part of the human or animal body.

Alternatively or in addition, the enclosed space may be illuminated by a light source configured to be disposed proximate the image acquisition apparatus. More specifically, the light source may be configured to receive a lens of the image acquisition apparatus such a light emitting part of the light source is disposed around the lens. Alternatively or in addition, the light source may comprise a light emitting part of annular form. The light emitting part may comprise a plurality of Light Emitting Diodes (LEDs) disposed in relation to each other in a generally square pattern.

Alternatively or in addition, the data acquisition apparatus may comprise a digital camera. More specifically, the digital camera may be a true colour digital camera. The true colour nature of the digital camera may be afforded by a characteristic of an optical lens disposed between the part of the human or animal body and an aperture of the digital camera.

Alternatively or in addition, the apparatus may be configured to control the camera in respect of at least one of: at least one RGB analogue gain; at least one of HSV values corresponding to RGB values; exposure time; a gain of the camera; gamma; white balance; light power; contrast; and saturation.

Alternatively or in addition, the method may further comprise: displaying the compensated digital colour image on display apparatus; and selecting a plurality of different areas on the compensated digital colour image. The plurality of different areas may be selected by an operator, e.g. by means of pointing at each area with a mouse and clicking.

More specifically, colour characteristics of the colours within the plurality of different selected areas may be conveyed to the pigment mixing apparatus, which is operative to mix a plurality of pigments of different colours in dependence on the colour characteristics to produce a plurality of mixed pigments. The colour characteristics may be Red, Blue and Yellow (RBY) values determined from the plurality of different selected areas, e.g. by means of processing apparatus. The plurality of mixed pigments may correspond respectively to colours within the plurality of different selected areas. At least one of the pigments may be paint.

Alternatively or in addition, the pigment mixing apparatus may comprise a plurality of pigment dispensers, each pigment dispenser containing a pigment of a different colour.

Different batches of pigment of a particular colour may be of a slightly different colour. Hence, it may be desired to provide for colour consistency from batch to batch. Therefore, alternatively or in addition, the method may further comprise determining a colour of a batch of pigment, e.g. a fresh batch, by means of colour determining apparatus. The colour determining apparatus may comprise apparatus, such as a spectrophotometer, that is operative to determine a bulk colour value (e.g. at a measurement location) for the pigment batch. The colour determining apparatus may be operative to determine the Red, Blue, Yellow (RBY) values of the pigment.

More specifically, the method may further comprise comparing the determined colour of the pigment with a predetermined colour, e.g. as determined by measuring the colour of another batch of pigment, such as the batch most recently present in the colour mixing apparatus.

Alternatively or in addition, the method may further comprise changing proportions of pigments of different colours used to produce a pigment mixture in dependence on the determined colour of the batch of pigment. Hence, for example, relative amounts of Red Blue and Yellow pigments used to form the plurality of mixed pigments may be changed to take account of a change in colour from one batch of pigments to another.

Alternatively or in addition, the method may further comprise: conveying the colour compensated digital colour image to printing apparatus; and printing the colour compensated digital colour image by means of the printing apparatus. The colour compensated digital colour image may be wirelessly conveyed to the printing apparatus.

More specifically, the method may further comprise acquiring by image acquisition apparatus an image of an image printed by the printing apparatus to provide a digital colour printed image. The image acquisition apparatus may comprise a digital camera. Preferably, a calibration transform may have been determined for the image acquisition apparatus. Hence, any contrary effect as regards colour caused by the image acquisition apparatus and/or lighting when the image acquisition apparatus is operative may be minimised. The printed image may comprise a colour chart, e.g. a colour chart stored in processing apparatus. The digital colour printed image, e.g. of the colour chart, may be conveyed to processing apparatus.

Alternatively or in addition, the method may comprise: determining a printer calibration transform for colours of an image, e.g. of a colour chart, printed by the printer; and transforming a colour compensated digital colour image in dependence on the printer calibration transform. Thus, the printer may print an image that properly reflects the true colours of the colour compensated digital colour image.

According to a second aspect of the present invention, there is provided apparatus for colouring a cosmetic covering, the apparatus comprising:

image acquisition apparatus operative to acquire an image of a part of a human or animal body to provide a digital colour image;

processing apparatus operative to determine a calibration transform for colours of an image acquired by the image acquisition apparatus, the processing apparatus being further operative to transform the digital colour image with the calibration transform to provide a colour compensated digital colour image;

pigment mixing apparatus operative to mix a plurality of pigments of different colours in dependence on at least one colour characteristic of at least one colour within the colour compensated digital colour image to produce at least one mixed pigment; and pigment applying apparatus operative to apply the at least one mixed pigment to a cosmetic covering.

The cosmetic covering may be configured to cover a prosthesis, such as a hand prosthesis. More specifically, the cosmetic covering may be a surface of the cosmetic covering. In one form, the at least one mixed pigments may be applied by a person, e.g. using a brush. In another form, the at least one mixed pigments may be applied by pigment applying apparatus, such as spray painting apparatus.

More specifically, the processing apparatus may comprise a computer, such as a Personal Computer (PC). The image acquisition apparatus may comprise a colour digital camera and may be configured to convey the digital colour image to the processing apparatus for processing thereon.

According to a third aspect of the present invention, there is provided a method of determining skin colour, the method comprising:
  determining a calibration transform for colours of an image acquired by image acquisition apparatus;
  acquiring an image of a part of a human or animal body with the image acquisition apparatus to provide a digital colour image; and
  transforming the digital colour image with the calibration transform to provide a colour compensated digital colour image.

Alternatively or in addition, the method may further comprise: displaying the compensated digital colour image on display apparatus; and selecting a plurality of different areas on the compensated digital colour image. The plurality of different areas may be selected by an operator, e.g. by means of pointing at each area with a mouse and clicking.

More specifically, colour characteristics of the colours within the plurality of different selected areas may be conveyed to the pigment mixing apparatus, which is operative to mix a plurality of pigments of different colours in dependence on the colour characteristics to produce a plurality of mixed pigments. The colour characteristics may be Red, Blue and Yellow (RBY) values determined from the plurality of different selected areas, e.g. by means of processing apparatus. The plurality of mixed pigments may correspond respectively to colours within the plurality of different selected areas. At least one of the pigments may be paint.

Alternatively or in addition, the method may further comprise applying the plurality of mixed pigments to a person. Thus, the method of the present invention may be used for applying make-up or for cosmetic tanning. Alternatively, the method of the present invention may be used for applying mixed pigments for cosmetic skin repair, e.g. for persons with burn scarred skin.

According to a fourth aspect of the present invention, there is provided apparatus for determining skin colour, the apparatus comprising:
  image acquisition apparatus operative to acquire an image of a part of a human or animal body to provide a digital colour image; and
  processing apparatus operative to determine a calibration transform for colours of an image acquired by the image acquisition apparatus,
  the processing apparatus being further operative to transform the digital colour image with the calibration transform to provide a colour compensated digital colour image.

More specifically, the processing apparatus may comprise a computer, such as a Personal Computer (PC). The image acquisition apparatus may comprise a colour digital camera and may be configured to convey the digital colour image to the processing apparatus for processing thereon.

Further embodiments of the second aspect of the present invention may comprise one or more features of the first aspect of the present invention.

BRIEF DESCRIPTION OF THE DRAWINGS

The present invention will now be described by way of example only with reference to the following drawings, of which.

SPECIFIC DESCRIPTION

Figure 1A:
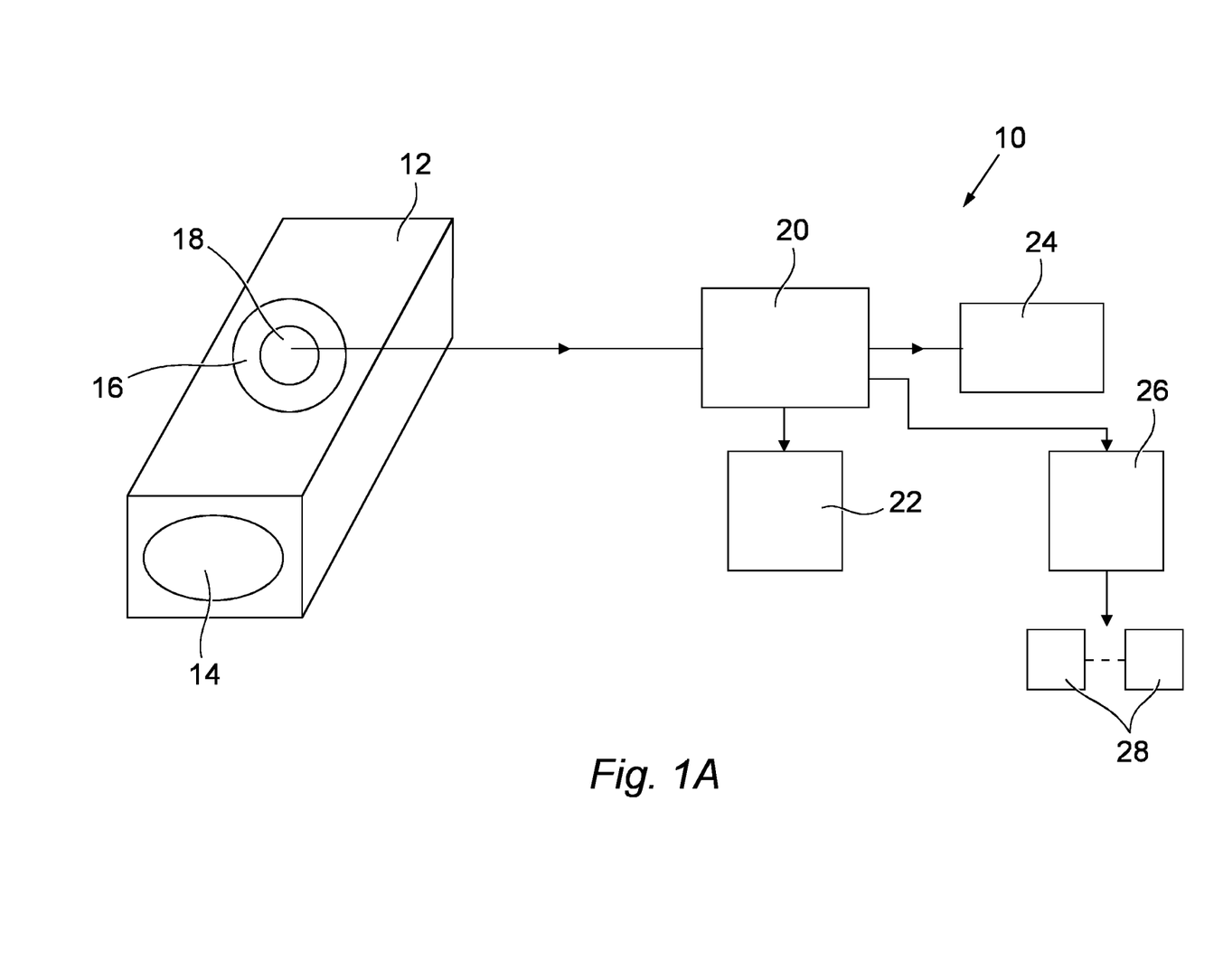
FIG. 1A is a diagram of apparatus according to the present invention.
Figure 1B:
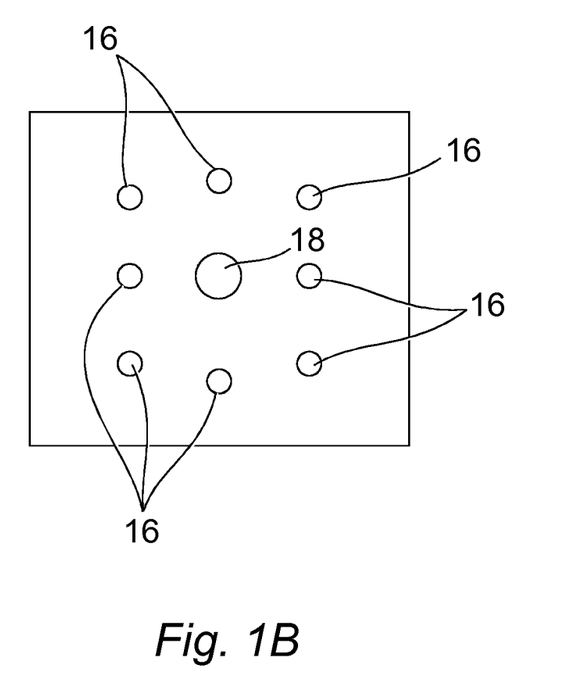
FIG. 1B shows the disposition of LEDs with respect to each other and the camera.

Apparatus for colouring a cosmetic covering 10 is shown in FIG. 1A. The apparatus 10 comprises an enclosure, which defines an entirely enclosed space, with the exception of an aperture 14 of sufficient size and shape to allow a part of body, such as a hand, to be received within the enclosure. At least most of the interior surface of the enclosure is white. The apparatus also comprises an arrangement of LEDs 16, each LED being an Osram Golden Dragon Plus, white, LW W5AM-JYKY-5K8L from Osram GmbH, Hellabrunner Strasse 1, 81543 Munchen, Germany, and a 9.1 MP digital colour camera 18, namely a microscope c mount camera MDCM-900 from Mueller Optronic of Am Hugel 10A, 99084 Erfurt, Germany. A 3 volt power supply provides electrical power for the LEDs. A 1 Ohm resistor is in series between each LED and the power supply. The digital colour camera 18 comprises a true colour low magnification video lens, namely a Navitar NMV-5WA standard C mount lens from Navitar Inc. of 200 Commerce Drive, Rochester N.Y. 14623, USA. The disposition of the LEDs 16 in relation to each other and the camera 18 is shown in FIG. 1B. As can be seen from FIG. 1B, the LEDs 16 form a generally square pattern with the camera 18 substantially at the centre of the square pattern. The camera and the LEDs are located in the roof of the enclosure such that the LEDs illuminate the interior of the enclosure and the camera is capable of acquiring an image of the body part located within the enclosure. An output from the digital colour camera 18 is electrically connected to a Personal Computer (PC) 20, which comprises a Visual Display Unit (VDU) 22. The Personal Computer is in communication with an Epson R2880 printer 24, with communication being either wired or wireless depending on whether the printer is in the same locale as the Personal Computer or at a distant location. Software running on the PC is operative to control and operate the camera 18. The software has been developed for Microsoft Windows XP or higher using Visual Studio 2008 and Direct Show SDK. The Direct Show SDK provide for the interface with the camera with camera set-up controls provided by Mueller Optronic. The software is operative to provide a hardware accelerated live view of the body part inside the enclosure and controls for adjusting the camera parameters. The controls are only displayed when the apparatus is in a set-up mode to thereby reduce the likelihood of the operator adjusting the controls so as to compromise proper operation of the apparatus. Likewise, the default control settings for the camera under particular lighting conditions are hard-coded into the software to reduce the likelihood of operator adjustments that might compromise proper operation of the apparatus. Design of such software is readily with the scope of the ordinary design skills of the person skilled in the art. The default control settings for the camera comprise the RGB (Red Green Blue) channel analogue gains, HSV (Hue Saturation and Value) representations of the RGB values, exposure time, the gain of the camera and gamma, contrast and saturation. The default control settings are determined by taking images of a Gretag MacBeth colour chart located in the enclosure and adjusting the control settings until the desired quality of image is obtained. The apparatus 10 further comprises paint mixing apparatus 26, which is operative to mix differently coloured pigments to provide a plurality of pigment mixtures 28. The differently coloured pigments are contained within a plurality of respective containers within the paint mixing apparatus. The containers are supported on a carousel arrangement so that each container is moved proximate a mixing container so that the container's contents may be dispensed into the mixing container. The contents of a container are dispensed by means of a syringe pump. Hence, the paint mixing apparatus 26 comprises a container for each of Red, Blue and Yellow, a container containing clear silicone and a container containing white silicone. When a particular colour is obtained, the mixture typically comprises about 80% clear silicone, about 18% white silicone and about 2% for each of the Red, Blue and Yellow. The design of the paint mixing apparatus is readily within the ordinary design skills of the person of skill in the art. The paint mixing apparatus 26 is in communication with the Personal Computer 20, with communication being either wired or wireless depending on whether the paint mixing apparatus is in the same locale as the Personal Computer or at a distant location.

Figure 2:
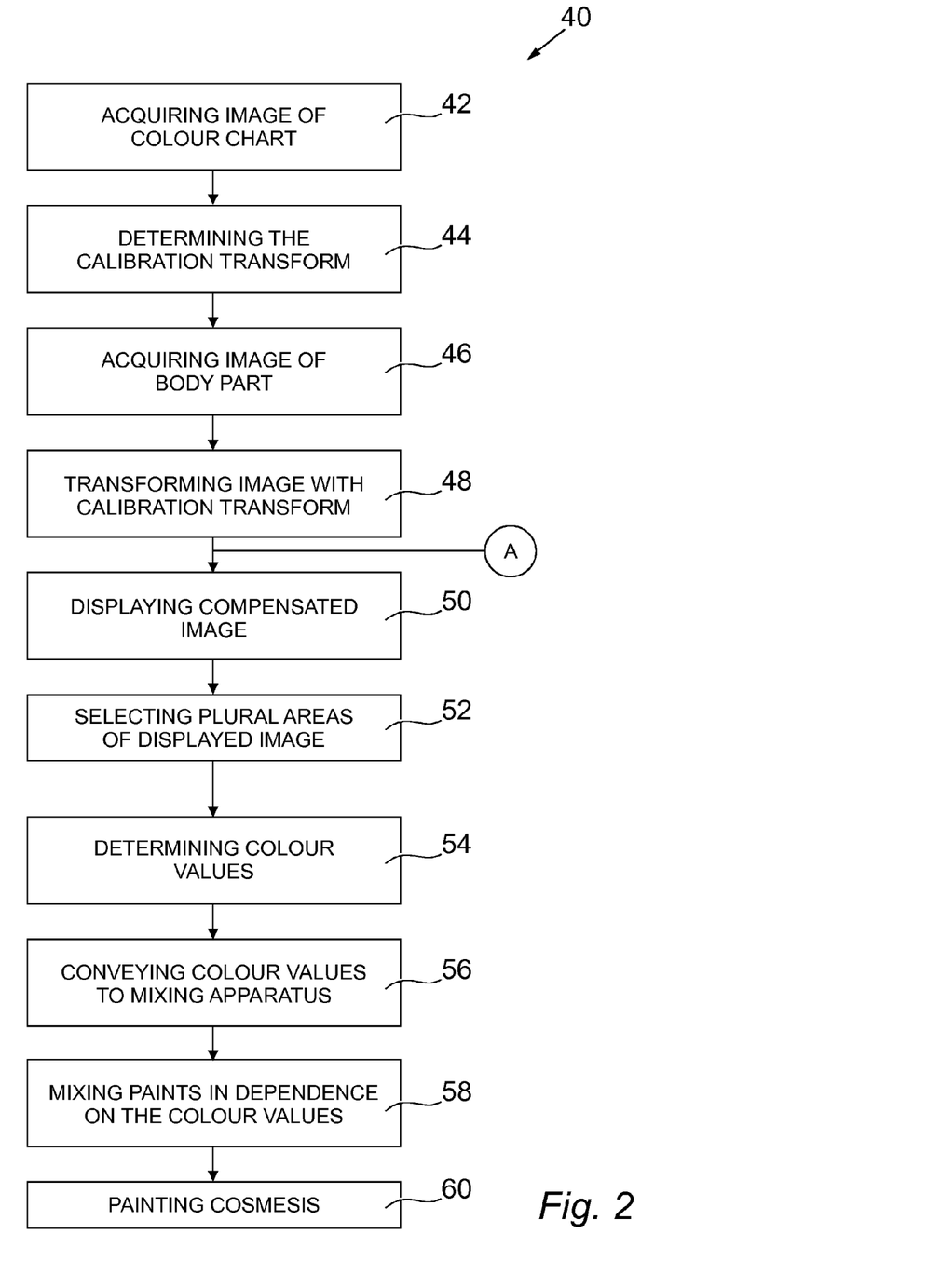
FIG. 2 is a flow chart representation of a method of colouring a cosmetic covering according to the present invention.

A method according to the present invention will now be described with reference to FIG. 2, which represents steps of the method in flow-chart form 40. A Munsell Colour XRite Gretag MacBeth colour chart is placed in the enclosure 12 of FIG. 1A and an image of the colour chart is acquired 42 by the digital colour camera 18. The colour chart image is conveyed to the Personal Computer (PC) 20. The PC is operative to determine a colour difference between each of the colour values in the colour chart image with each corresponding actual colour value for the colour chart stored in the PC. Each colour difference is translated into RGB positional space (3D colour space) such that the colour differences are in the form of sparse points in a Look Up Table (LUT) for each of Red, Green and Blue values. The PC is operative to interpolate between the sparse points in each LUT with a Catmull-ROM point fitting curve being used. The resulting LUT values are filtered by means of a rolling average filter with twelve taps. The thus determined LUTs are used to effect a calibration transformation of subsequently acquired images to thereby compensate for inaccuracies in the colour representation arising from acquisition by the digital colour camera. In other words, transformation of the colour chart image with the LUT based calibration transform produces a compensated colour chart image that more faithfully represents the true colours contained in the colour chart.

The calibration transform may also include determining calibrations for one or more of the group comprising: light power, based on the perceived brightness of one or more greyscale values; saturation; gamma function; and contrast function.

The camera 18 may also include an auto white balance to compensate for variation in camera sensitivity. The step of compensating for the variation in camera sensitivity may be performed before the brightness calibration is determined and corrected.

The calibration transform may satisfy the requirements of an industry standard profile, such as those set by the International Colour Consortium (ICC). This is termed a colour model of the camera response.

Figure 5:
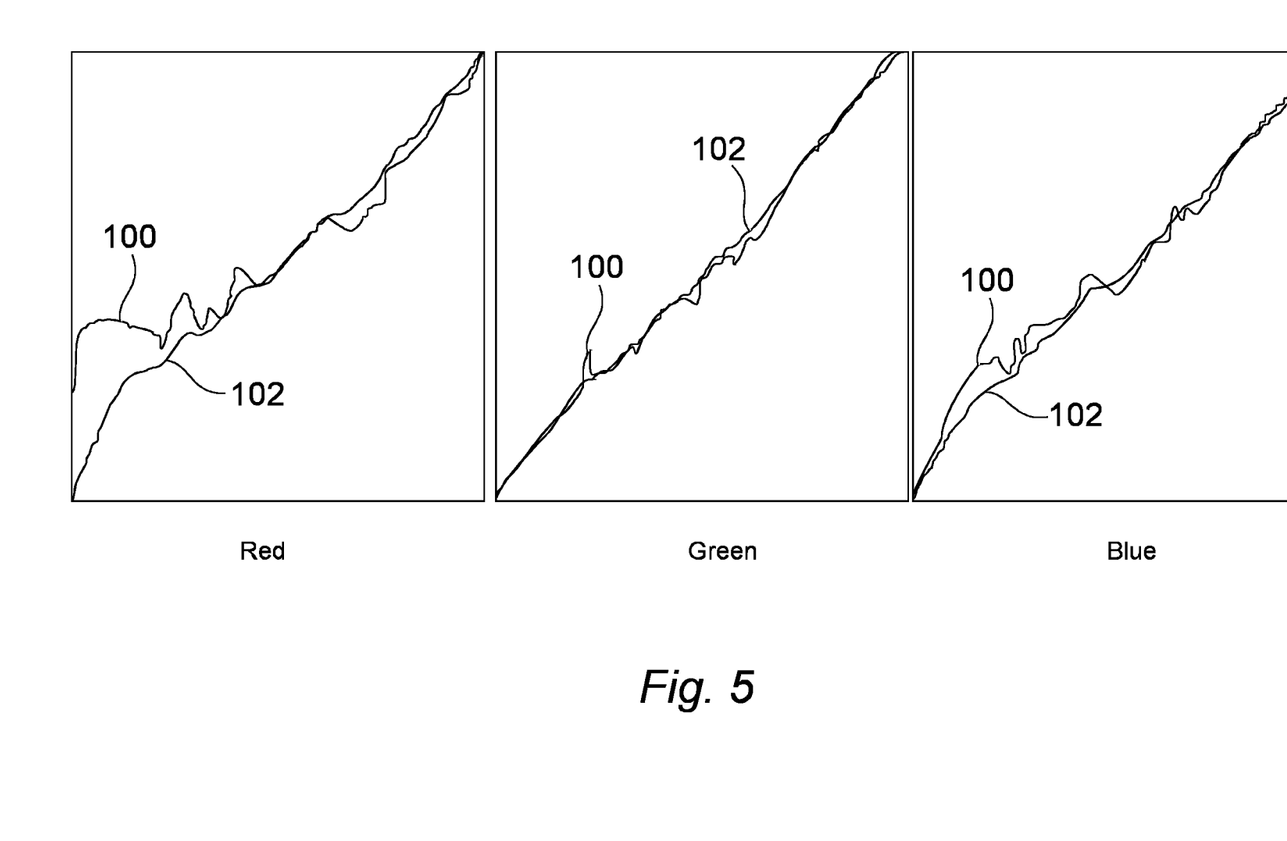
FIG. 5 shows un-transformed and transformed RGB curves.

Un-transformed and transformed RGB curves are shown in FIG. 5. In FIG. 5, the un-transformed curves for each of Red, Green and Blue are indicated by reference numeral 100 and the transformed curves are indicated by reference numeral 102. As can be seen, transformed curves are closer to the ideal straight, diagonal line than the un-transformed curves. The above described calibration procedure is normally only carried out at a conclusion to manufacture of apparatus according to the invention. However, the calibration procedure may be carried out in the field if the configuration of the apparatus is changed, e.g. if there is a change in lighting conditions or if there is a change in ambient temperature that is sufficient to warrant re-calibration.

Referring again to FIG. 2, the wearer of a prosthetic right hand places his left hand in the enclosure 12 of FIG. 1A. The digital colour camera is operative to acquire a series of images at a sampling rate of about one second. The series of images are displayed on the VDU 22 by way of the PC 20. A clinician inspects the displayed images to determine whether or not a full image of the hand is displayed and whether or not the hand is properly oriented within the enclosure. If not, the wearer moves his hand within the enclosure to remedy the lack of proper positioning. When the hand is positioned properly, operator operates the PC, e.g. by means of a "capture" button on the software interface, such that the digital colour image displayed at that time is stored in the PC. Then the PC 20 is operative to transform the stored digital colour with the calibration transform to produce a compensated digital colour image 48. Further images of the hand, e.g. bottom and side images, may then be acquired and transformed as described above and depending on requirements. Thereafter the compensated digital colour image is displayed on the VDU 50 and the clinician, or painter, selects six to ten different areas on the image 52. The PC is then operative to determine the colour values of the selected areas in terms of Red, Blue, Yellow (RBY) values for the selected areas 54. Alternatively, RBY colour values may be determined on the basis of a predetermined recipe and without the clinician selecting the different areas. The colour values are conveyed 56 to the paint mixing apparatus 26 and the paint mixing apparatus 26 is operative to produce paint mixtures of the correct colour 58 in dependence on the received colour values. When the paint mixing is complete, the clinician, or painter, paints the surface of the cosmetic covering with the paint mixtures 60. Data for acquired images and corresponding colour values are encrypted to reduce the likelihood of tampering and the proper operation of the apparatus being compromised.

Figure 3:
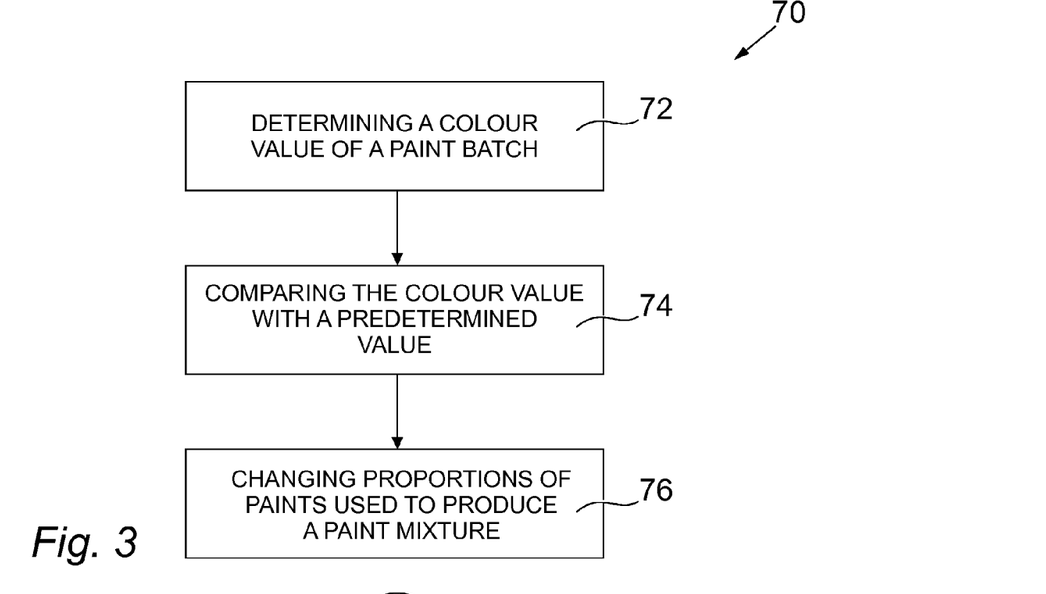
FIG. 3 is a flow chart representation of a method of compensating for variation in pigment colours.

The colour of paint of a particular colour may vary from batch to batch. Hence and referring to FIG. 3, the colour value of a fresh batch of paint is determined with a spectrophotometer 72. A colour value determined by the spectrophotometer is conveyed to the PC 20, which stores a desired colour value for the particular colour in question, e.g. a colour value for a previously used batch of paint of the same colour. The PC is operative to compare the spectrophotometer determined colour value with the stored colour value 74 and to change a compensated digital colour image (see step 48 in FIG. 2) to take account of a variation in the colour value. Hence, when the paint mixing apparatus 26 is operative to mix paints in dependence on the compensated digital colour image variations in paint colour from batch to batch can be compensated for.

Figure 4:
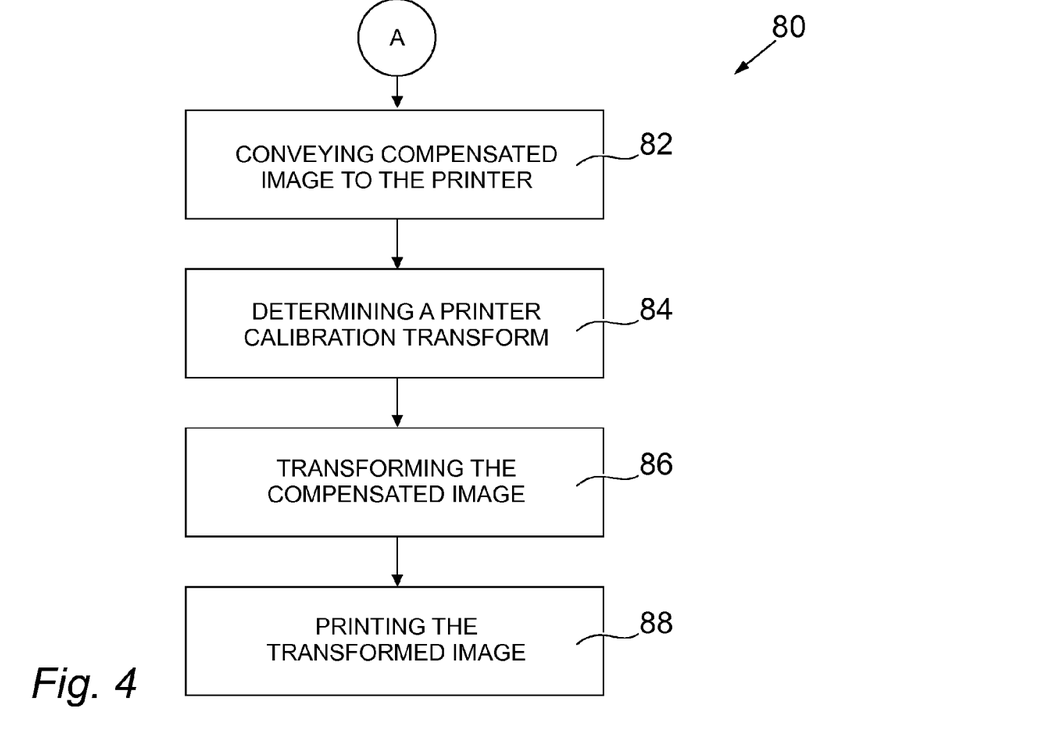
FIG. 4 is a flow chart representation of a method of colour compensating a printer.

It is often desirable to provide a printed copy of an acquired image of wearer's hand, e.g. for the purposes of the clinician or for inspection by the wearer himself. The International Colour Consortium (ICC) colour profile for the Epson R2880 printer 24 is set for Premium Luster paper as the default Image Colour Management (ICM) profile upon conclusion of manufacture of apparatus according to the invention. During use, the ICM settings provide for faithful printing of stored images. However, the printer 24 may be liable under certain circumstances to introduce errors in the reproduction of the colours of the acquired image. Therefore, calibration may be desired. Hence and referring to FIG. 4 a true Gretag MacBeth colour chart stored in the PC 20 is printed with the printer 24, 82. Then the digital colour camera 18 is used to acquire an image of the printed image and the acquired image is conveyed to the PC. The colour values in the acquired image of the colour chart are compared with the respective colour values in the stored colour chart. The PC is then operative to determine a printer calibration transform 84 in dependence on the colour value comparisons, with the printer calibration transform being effective to compensate for inaccuracies in the colour representation arising from printing with the printer. Hence and referring to step 48 in FIG. 2, a compensated image of the wearer's hand is conveyed to the printer 82, the compensated image is transformed with the printer calibration transform 88 to take account of printer inaccuracies and the further compensated image is printed with the printer 88.

Following calibration of the camera as is described above, an image of a Gretag MacBeth colour chart was acquired and printed. A spectrophotometer was used to determine colour values for each colour patch of the Gretag MacBeth colour chart and of the printed image of the Gretag MacBeth colour chart and the differences between corresponding values in the two sets of measurements were determined. The mean sum of the absolute differences was then determined to thereby provide a percentage error for the printed image as a whole. By following this procedure, the apparatus according to the invention was shown to have an error of substantially 5.76%. It should be noted that it is undesirable for the calibration transform to provide for ideal calibration, i.e. such that the values in each LUT describe a straight, diagonal line. This is because ideal calibration may involve RGB values becoming negative, i.e. the values may become de-saturated, with the consequence that image quality is reduced.

The apparatus and method according to the present invention may be employed in other applications. For example, the apparatus and method may be used in the cosmetics industry or in medical diagnosis. More specifically, the apparatus may be used to compare skin before and after the application of cosmetics to provide feedback to a user as to the appropriateness of the cosmetics applied. Alternatively, the apparatus may be used to detect skin colour profiles that are indicative of disease. An ultraviolet camera may be used instead of the colour camera 18 of FIG. 1A to see below the surface of the skin. Such an ultraviolet camera may be particularly useful in detecting skin conditions that are not evident from an inspection of the skin surface.

The invention claimed is:

1. A method of colouring a cosmetic covering, the method comprising:
   acquiring an image of a colour chart with image acquisition apparatus to provide a colour chart image;
   determining a calibration transform for colours of an image acquired by image acquisition apparatus in dependence on the colour chart image and colour values represented in the colour chart, wherein the calibration transform includes transformations for each of Red, Green and Blue values and each Red, Green and Blue transformation includes a Look Up Table (LUT), wherein each LUT is determined by sparsely populating the LUT with colour differences between each of the colour values in the colour chart image and each corresponding actual colour for the colour chart and interpolating between the sparse points;
   acquiring an image of a part of a human or animal body with the image acquisition apparatus to provide a digital colour image;
   transforming the digital colour image with the calibration transform to provide a colour compensated digital colour image;
   conveying at least one colour characteristic of at least one colour within the colour compensated digital colour image to a pigment mixing apparatus, which is operative to mix a plurality of pigments of different colours in dependence on the at least one colour characteristic to produce at least one mixed pigment; and
   applying the at least one mixed pigment to a cosmetic covering.

2. A method according to claim 1, wherein the cosmetic covering is configured to cover a prosthesis.

3. A method according to claim 1 comprising acquiring a plurality of different images of the part of the human or animal body.

4. A method according to claim 1 further comprising the step of disposing the part of the human or animal body in relation to the image acquisition apparatus and displaying an image of the part acquired by the image acquisition apparatus on display apparatus, the step being carried out before the step of acquiring an image of the part to provide the digital colour image.

5. A method according to claim 1, wherein the human or animal body part is illuminated by a light source configured to provide for substantially uniform illumination in a plane extending generally perpendicular to a path between the image acquisition apparatus and the part of the human or animal body.

6. A method according to claim 5, wherein the light source is configured to receive a lens of the image acquisition apparatus such that a light emitting part of the light source is disposed around the lens.

7. A method according to claim 1, wherein the light source comprises a light emitting part of annular form.

8. A method according to claim 1, wherein the data acquisition apparatus comprises a digital camera.

9. A method according to claim 8, wherein the apparatus is configured to control the camera in respect of at least one of: at least one RGB analogue gain; at least one of HSV values corresponding to RGB values; exposure time; a gain of the camera; gamma; contrast; and saturation.

10. A method according to claim 1, wherein the method further comprises:
    displaying the compensated digital colour image on display apparatus; and selecting a plurality of different areas on the compensated digital colour image.

11. A method according to claim 10, wherein colour characteristics of the colours within the plurality of different selected areas are conveyed to the pigment mixing apparatus to produce a plurality of mixed pigments.

12. A method according to claim 11 further comprising applying the plurality of mixed pigments to the cosmetic covering.

13. A method according to claim 1, wherein the pigment mixing apparatus comprises a plurality of pigment dispensers, each pigment dispenser containing a pigment of a different colour.

14. A method according to claim 13 further comprising determining a colour of a batch of pigment by means of colour determining apparatus, the colour determining apparatus comprising apparatus that is operative to determine a bulk colour value for the pigment batch.

15. A method according to claim 14 further comprising comparing the determined colour of the pigment with a predetermined colour.

16. A method according to claim 14 further comprising changing proportions of pigments of different colours used to produce a pigment mixture in dependence on the determined colour of the batch of pigment.

17. A method according to claim 1 further comprising: conveying the colour compensated digital colour image to printing apparatus; and printing the colour compensated digital colour image by means of the printing apparatus.

18. A method according to claim 17 further comprising acquiring by image acquisition apparatus an image of an image printed by the printing apparatus to provide a digital colour printed image.

19. A method according to claim 18 further comprising: determining a printer calibration transform for colours of an image printed by the printer; and transforming a colour compensated digital colour image in dependence on the printer calibration transform.

20. An apparatus for colouring a cosmetic covering, the apparatus comprising:
 an image acquisition apparatus operative to acquire an image of a colour chart to provide a colour chart image and an image of a part of a human or animal body to provide a digital colour image;
 a processing apparatus operative to determine a calibration transform for colours of an image acquired by the image acquisition apparatus in dependence on the colour chart image and colour values represented in the colour chart, wherein the calibration transform includes transformations for each of Red, Green and Blue values and each Red, Green and Blue transformation includes a Look Up Table (LUT), wherein each LUT is determined by sparsely populating the LUT with colour differences between each of the colour values in the colour chart image and each corresponding actual colour for the colour chart and interpolating between the sparse points, the processing apparatus being further operative to transform the digital colour image with the calibration transform to provide a colour compensated digital colour image;
 a pigment mixing apparatus operative to mix a plurality of pigments of different colours in dependence on at least one colour characteristic of at least one colour within the colour compensated digital colour image to produce at least one mixed pigment; and
 a pigment applying apparatus operative to apply the at least one mixed pigment to a cosmetic covering.

21. An apparatus according to claim 20, wherein the cosmetic covering is configured to cover a prosthesis.

22. An apparatus according to claim 20 comprising a computer and in which the image acquisition apparatus comprises a colour digital camera and is configured to convey the digital colour image to the processing apparatus for processing thereon.

* * * * *